United States Patent [19]
Nohira et al.

[11] Patent Number: 4,891,519
[45] Date of Patent: Jan. 2, 1990

[54] PHOTOMETERING APPARATUS

[75] Inventors: Tadashi Nohira, Chiba; Tsuneo Imatsu, Misato; Ikuzo Kagami, Tokyo, all of Japan

[73] Assignee: Komatsugawa Chemical Engineering Co., Ltd., Tokyo, Japan

[21] Appl. No.: 257,635

[22] Filed: Oct. 14, 1988

[30] Foreign Application Priority Data

Oct. 19, 1987 [JP]  Japan .................................. 62-261774

[51] Int. Cl.$^4$ .......................... G01J 1/42; G01N 21/82
[52] U.S. Cl. .................................... 250/349; 356/442; 250/573
[58] Field of Search ............... 250/349, 341, 573, 574, 250/576, 564, 565, 357.1; 356/441, 442; 374/17

[56] References Cited

U.S. PATENT DOCUMENTS

| | | | |
|---|---|---|---|
| 4,072,424 | 2/1978 | McMullan et al. | 250/573 |
| 4,319,138 | 3/1982 | Sweet | 250/576 |
| 4,695,734 | 9/1987 | Aonma et al. | 250/573 |
| 4,725,148 | 2/1988 | Endo et al. | 356/442 |

FOREIGN PATENT DOCUMENTS

0226834  12/1984  Japan .................................... 250/349

*Primary Examiner*—Janice A. Howell
*Assistant Examiner*—Richard Hanig

*Attorney, Agent, or Firm*—Spencer & Frank

[57] ABSTRACT

A turbidimeter for measuring a turbidity of a test liquid including a hollow main body having openings formed at its lower end through which the test liquid is introduced into a measuring optical path within the main body, a semiconductor laser diode arranged in the main body at its upper end and emitting a laser light, a first prism arranged within the main body and guiding the laser light into the measuring optical path, a second prism arranged within the main body and guiding light emanating from the measuring optical path to the upper end of the main body, first and second semiconductor photodiodes arranged within the main body at its upper end such that the light emanating from the second prism is exclusively made incident upon the first semiconductor photodiode, and first and second operational amplifiers arranged within the main body at its upper end and amplifying output signals supplied from the first and second semiconductor photodiodes, respectively. Output signals generated from the first and second operational amplifiers are supplied to a differential amplifier to derive a difference therebetween, the difference corresponding to the turbidity of the test liquid. The differential amplifier is arranged remote from the main body, so that any error in the measured turbidity due to the temperature variation can be compensated for.

12 Claims, 8 Drawing Sheets

FIG_1A
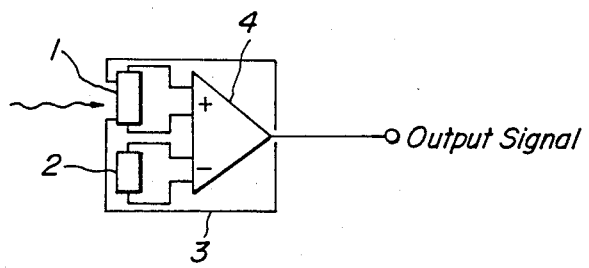
FIG_1B
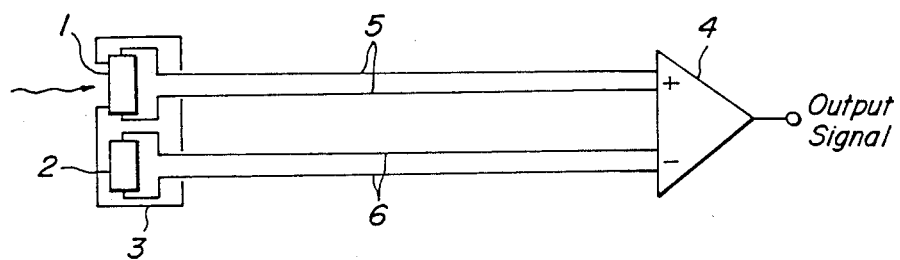

FIG_3

FIG_6
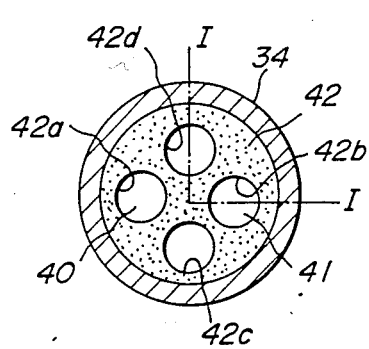
FIG_7
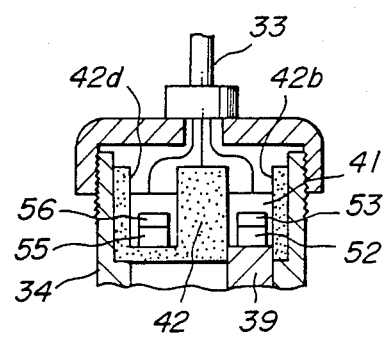
FIG_11
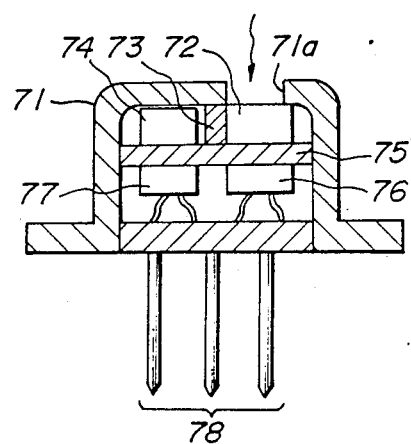

FIG_8
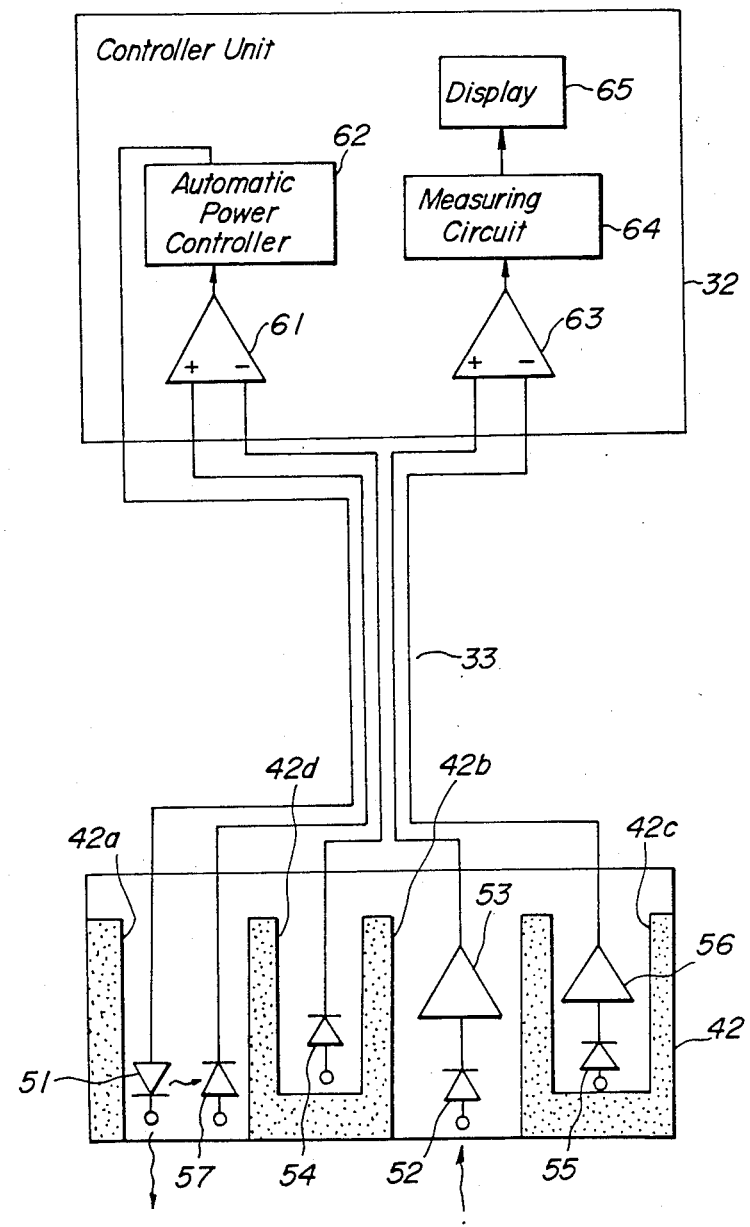

FIG_9A
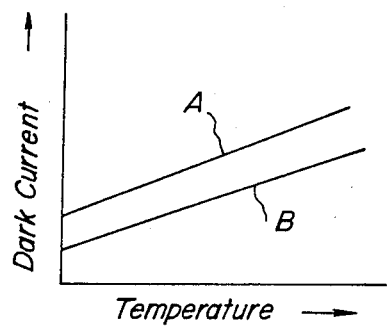
FIG_9B
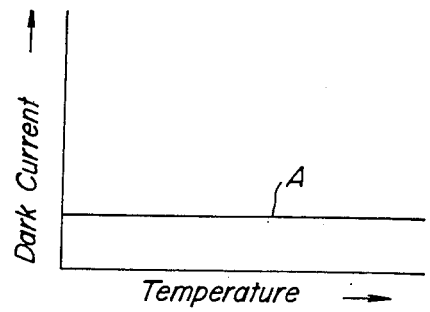

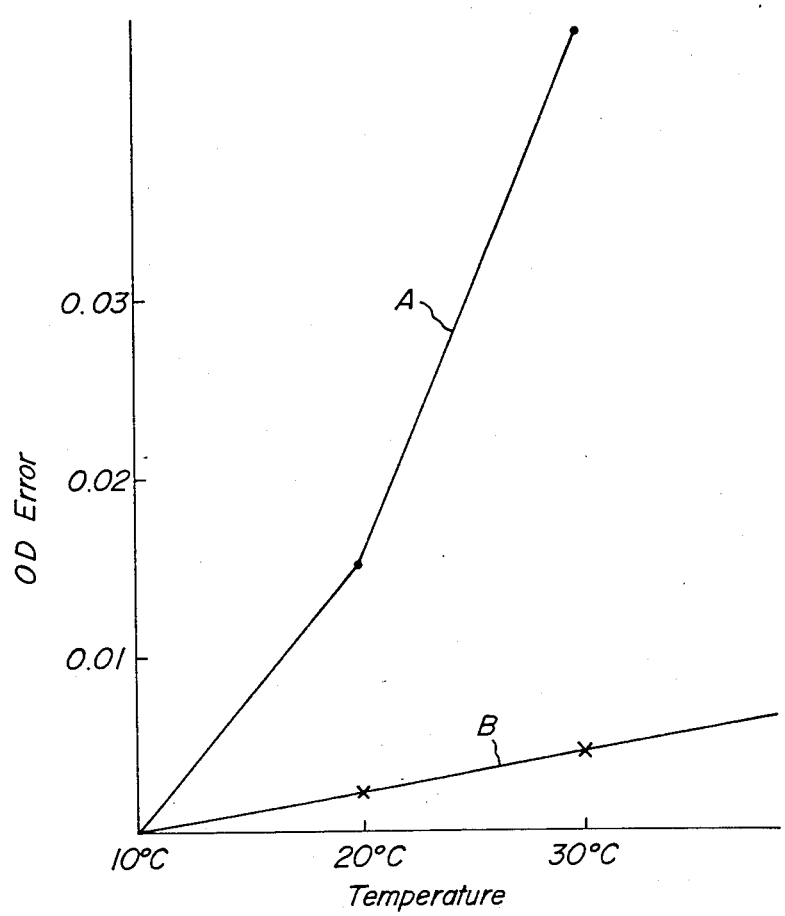
FIG_10

PHOTOMETERING APPARATUS

BACKGROUND OF THE INVENTION

1. Field of the Invention and Related Art Statement

The present invention relates to a photometering apparatus comprising a light emitting portion including a light emitting element for projecting a radiation beam to a substance to be measured, and a light receiving portion including a light receiving element for receiving radiation emanating from the substance and converting it into an electric signal.

The above mentioned photometering apparatus has been widely used in various kinds of photometries, particularly in a turbidimeter for measuring the turbidity of a particle suspension and in a colorimeter for measuring the absorbance of a test solution for radiation having a specified wavelength. For instance, in Japanese Patent Application Laid-open Publication, Kokai-Sho 60-259,935 (corresponding to U.S. Pat. No. 4,725,148) there is disclosed a turbidimeter including a semiconductor laser diode serving as the light emitting element and a semiconductor photodiode serving as the light receiving element. Such a turbidimeter is preferably used in the fermentation apparatus for measuring the turbidity of a culture solution. In case of using the semiconductor photodiode as the light receiving element, there is produced a measurement error due to the variation of the operation temperature of the semiconductor photodiode. In order to avoid such a drawback, in FIG. 5 of said publication the temperature compensation is effected by amplifying an output signal of the semiconductor photodiode by an operation amplifier with a negative feedback.

In the turbidimeter having the temperature compensating means disclosed in the above mentioned publication, the turbidity can be measured with the precision of first order below the decimal point, i.e. $10^{-1}$, but can not be measured with much higher precision such as second and third order below the decimal point ($10^{-2}$ and $10^{-3}$). In the recent turbidimetry for use in the fermentation apparatus, it is earnestly required to provide the turbidimeter which can measure the turbidity very accurately with the precision of the third order below the decimal point so that the variation of the culture solution within a short time period can be detected precisely.

In order to effect the temperature compensation much more accurately, the inventors of the instant application had devised experimentally a turbidimeter shown in FIG. 1A in which in addition to a first semiconductor photodiode 1 there is provided a second semiconductor photodiode 2 having the same construction as the first semiconductor photodiode, said first and second semiconductor photodiodes 1 and 2 being installed in a single housing 3, while the second semiconductor photodiode 2 being shielded from light, and a difference between output signals from the first and second semiconductor photodiodes 1 and 2 is derived by a differential amplifier 4. In this turbidimeter, since the operational temperatures of the first and second semiconductor photodiodes 1 and 2 are identical with each other, the temperature compensation can be effected by subtracting the dark current of the second semiconductor photodiode 2 from the output signal from the first semiconductor photodiode 1. However, the temperature variation of the differential amplifier 4 for deriving the difference between the output signals from the first and second semiconductor photodiodes could not be compensated sufficiently, so that the output signal from the differential amplifier 4 contains an erroneous component due to the temperature variation. In this manner, the measuring accuracy could not be improved even by using the turbidimeter illustrated in FIG. 1A. Particularly, the temperature drift of the differential amplifier 4 shows the non-linearity and the measurement error increases when the temperature becomes higher.

In order to mitigate the above explained drawback, the inventors further devised a turbidimeter shown in FIG. 1B. In this turbidimeter, the first semiconductor photodiode 1 and the second semiconductor photodiode 2 which is shielded from the external light are arranged in the same housing 3, and the output signals from these semiconductor photodiodes are supplied via signal conductors 5 and 6 to the differential amplifier 4 which is arranged at a position which is remote from the housing 3 and is not affected by the temperature variation. In this turbidimeter, the temperature drift of the semiconductor photodiode can be sufficiently canceled out and the temperature drift of the differential amplifier 4 can be suppressed. However, the long signal conductors 5 and 6 catch noises, and thus S/N of the output signal of the differential amplifier is decreased to an inadmissible extent. Since the impedance of the semiconductor photodiodes is rather high, the signal conductors 5 and 6 are liable to pick-up noises.

2. Summary of the Invention

The present invention has for its object to provide a novel and useful photometering apparatus, in which the temperature drift of the light receiving elements and amplifier can be compensated for sufficiently, while S/N of the output signal can be made high, so that the photometry can be carried out very accurately.

According to the invention, in a photometering apparatus including a light emitting portion having a light emitting element for projecting a radiation beam to a substance to be measured, and a light receiving portion having a first light receiving element for receiving radiation emanating from the substance and converting it into an electric signal, the improvement comprises a second light receiving element which has the same construction as that of the first light receiving element; a housing in which said first and second light receiving elements are installed such that the first light receiving element receives the radiation emanating from the substance, but the second light receiving element does not receive said radiation; first and second operational amplifiers having the same construction and being arranged in said housing, said first and second operational amplifiers being connected to receive and amplify output signals from the first and second light receiving elements to derive first and second amplified output signals, respectively; and a differential amplifier arranged remote from the housing and having first and second input terminals connected to said first and second operational amplifiers and deriving a difference between said amplified first and second output signals as a photometered output signal.

DESCRIPTION OF THE DRAWINGS

FIGS. 1A and 1B are schematic views showing photometering apparatuses which were experimentally devised by the inventors of the present application;

FIGS. 5 and 6 are lateral cross sections cut along lines I—I and II—II, respectively in FIG. 4;

FIG. 7 is a lateral cross section cut along a line I—I in FIG. 6;

FIG. 8 is a circuit diagram showing the connection of electric elements;

FIGS. 9A and 9B are graphs representing the operation for compensating the temperature drift;

FIG. 10 is a graph illustrating the variation of OD value due to the temperature variation; and FIG. 11 is a cross sectional view showing another embodiment of the photometering apparatus according to the invention.

DESCRIPTION OF THE PREFERRED EMBODIMENTS

Figure 2:
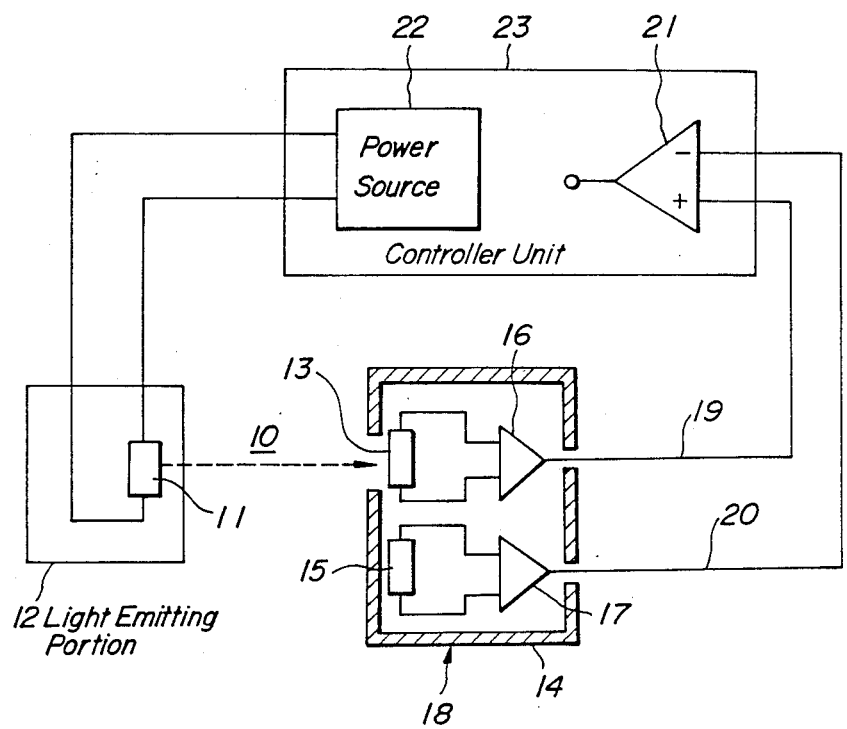
FIG. 2 is a schematic view illustrating the principal construction of the photometering apparatus according to the invention.

FIG. 2 shows the principal construction of the photometering apparatus according to the invention. The photometering apparatus comprises a light emitting portion 12 having a light emitting element 11 for projecting a radiation beam into a substance 10 whose turbidity or absorbance is to be measured, and a light receiving portion 18 having a first light receiving element 13 for receiving radiation which is transmitted or scattered through or by the substance 10, a second temperature compensating light receiving element 15 which has the same construction as that of the first light receiving element 13 and is arranged in the same housing 14, in which the first light receiving element is installed, in such manner that the second light receiving element does not receive radiation from the external, and first and second operational amplifiers 16 and 17 having the same construction, being arranged in said housing 14 and amplifying output signals supplied from the first and second light receiving elements 1 and 15, respectively. Output signals generated from the first and second operational amplifiers 16 and 17 are supplied via signal conductors 19 and 20 to a differential amplifier 21 for deriving a difference between the output signals. The differential amplifier 21 is arranged in a controller unit 23 together with a power supply source 22 for the light emitting element 11. The controller unit 23 is arranged remote from the light receiving portion 18.

According to the invention, the first light receiving element 13 receiving the radiation emanating from the substance 10 to be measured and the second light-shielded light receiving element 15 shielded from the external light are arranged in the same housing 14, so that their operational temperatures of these elements becomes identical with each other. Further, the output signals supplied from the light receiving elements 13 and 15 are amplified by the operational amplifiers 16 and 17 which have the identical construction and are arranged in the same housing 14, so that the temperature drift equally appears on the output signals supplied from the first and second operational amplifiers 16 and 17. Therefore, when the difference between the output signals supplied from the operational amplifiers 16 and 17 is derived, the temperature drifts of the light receiving elements 13 and 15 as well as the operational amplifiers 16 and 17 are canceled out. Further the signal conductors 19 and 20 are connected to the operational amplifiers 16 and 17 having a low output impedance, so that these conductors hardly pick-up noises. Moreover, if the noise is equally superimposed on the output signals transmitting through the signal conductors, the noise is generally canceled by the differential amplifier 21. In this manner, according to the invention the optical condition of the substance can be measured very precisely. Particularly, when the photometering apparatus according to the invention is applied to the turbidimeter, the turbidity can be measured very precisely with the precision of the third order below the decimal point.

Figure 3:
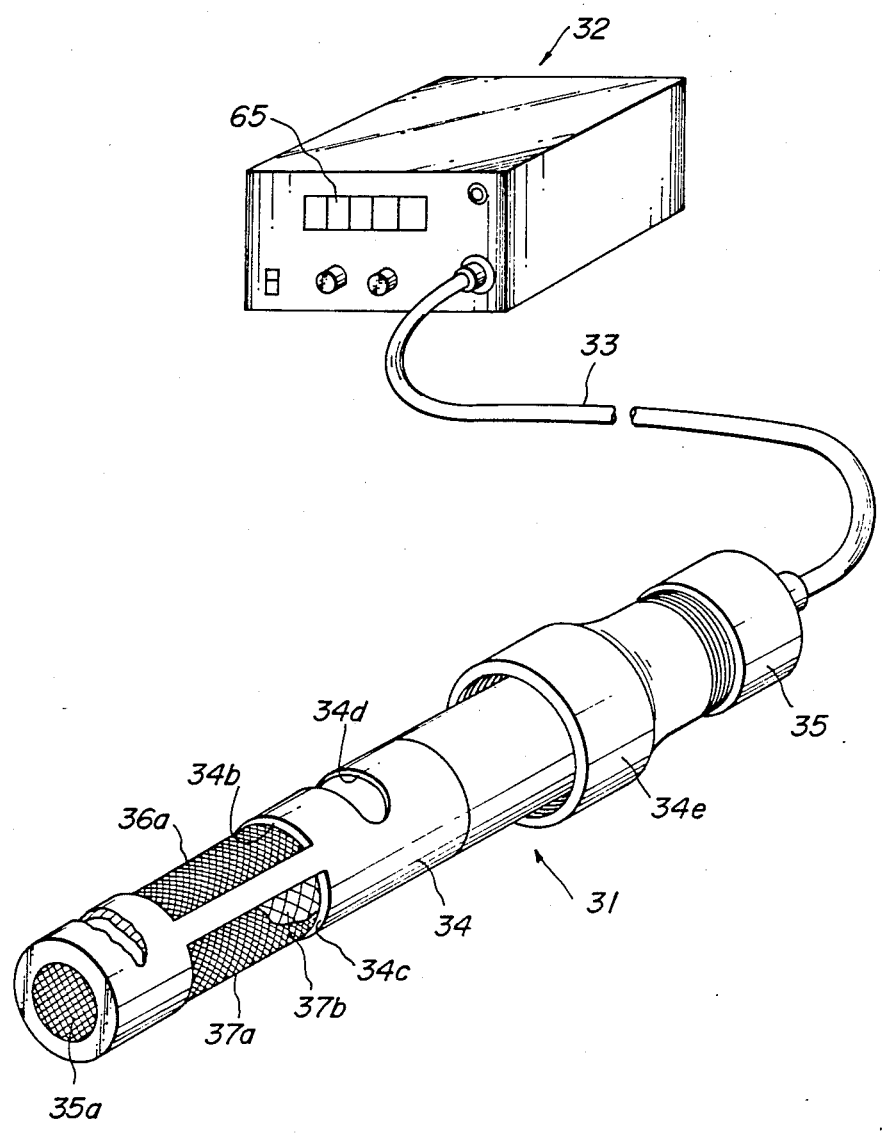
FIG. 3 is a perspective view depicting an embodiment of the turbidimeter including the photometering apparatus according to the invention.
Figure 4:
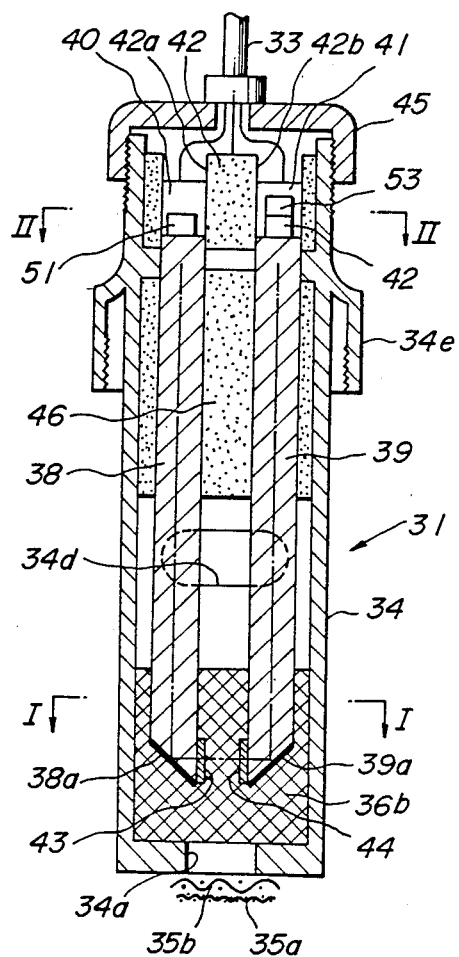
FIG. 4 is a longitudinal cross section showing the construction of the sensor unit shown in FIG. 3.
Figure 5:
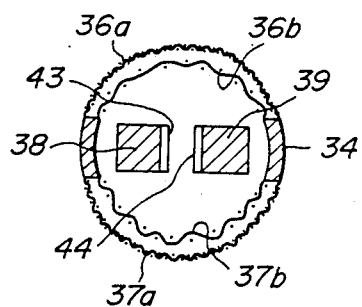

FIG. 3 is a perspective view illustrating the whole construction of an embodiment of the photometering apparatus which is constructed as the turbidimeter, FIG. 4 is a longitudinal cross section showing the sensor unit thereof, FIGS. 5 and 6 are lateral cross sections cut along lines I—I and II—II in FIG. 4, and FIG. 7 is a circuit diagram depicting the electrical connection. The turbidimeter comprises a sensor unit 31 and a controller unit 32 which are connected to each other by means of a signal cable 33. The sensor unit 31 comprises a hollow main body 34 formed by a metal cylinder in which a test solution whose turbidity is to be measured is introduced. To this end, the main body 34 has a circular opening 34a formed in its lower end surface and rectangular openings 34b and 34c formed in a side wall such that they are diametrically faced to each other. In the openings 34a, 34b and 34c there are arranged outer fine metal meshes 35a, 36a and 37a and inner coarse metal meshes 35b, 36b and 37b, respectively. These meshes are formed by yarning a thin metal wire, and the outer fine meshes 35a, 36a and 37a have 200 mesh and inner coarse meshes 35b, 36b and 37b have 60 mesh. The outer and inner meshes are brought into contact with each other.

The main body 34 further includes an opening 34d, but any mesh is not arranged in this opening 34d. Within the main body 34, elongated prisms 38 and 39 each formed by a rod made of material having a poor thermal conductivity such as glass, quartz, and plastics or by a fiber rod are arranged in parallel with the longitudinal axis. On an upper surface of the prism 38 is arranged a light emitting portion 40 including a semiconductor laser diode, and on an upper surface of the prism 39 is provided a light receiving portion 41 comprising semiconductor photodiodes. The light emitting portion 40 and the light receiving portion 41 are inserted into holes formed in a housing 42 made of insulating material having a good thermal conductivity. When the prisms 38 and 39 are formed by rods other than the optical fiber rods, it is preferable to apply reflecting films made of a metal such as aluminum on substantial parts of their side walls. At a lower portion of the prism 38 there is formed an inclined reflection surface 38a, so that infra-red laser light beam emitted from the semiconductor laser diode and made incident upon the prism 38 is reflected in the horizontal direction by the reflection surface 38a and is projected into the test liquid by means of a diffusion plate 43. The laser light beam transmitted through the test liquid is made incident via a diffusion plate 44 upon a reflection surface 39a which reflects the beam upwards. Conductors connected to the light emitting portion 40 and the light receiving portion 41 are extended out of the main body 34 by means of a hole formed in a cap 45 which is screwed to an upper end of the main body, and are connected to the controller unit 32 by means of the signal cable 33. A screw 34e is integrally formed with the main body 34 in order to fix the main body to a tube formed in a fermentation vessel. The prisms 38 and 39 are fixed in position within the main body 34 with the aid of a filling agent 46 made of synthetic resin.

In the present embodiment, a width of a measuring optical path defined by the mutually opposing diffusion plates 43 and 44 is set to 2 mm and a longitudinal and lateral dimensions of the optical path are set to 2.5 mm and 2.2 mm, respectively.

As shown in FIGS. 6 and 7 in detail, in the housing 42 there are formed two through holes 42a, 42b and two blind holes 42c, 42d. In the through hole 42a there is inserted the light emitting portion 40 including a semiconductor laser diode 51 (see FIG. 4) in such a manner that the laser light beam emitted from the semiconductor laser diode is made directly incident upon the prism 38. In the through hole 42b there is inserted the light receiving portion 41 including semiconductor photodiode 52 and operational amplifier 53 such that the laser light beam emanating from the prism 39 is made directly incident upon the semiconductor photodiode. In the blind hole 42c there is inserted a temperature compensating diode 54 (see FIG. 8) for compensating the variation or drift of the output power of the semiconductor laser diode 51 due to the temperature variation. In the blind hole 42d there are inserted temperature compensating semiconductor photodiode 55 having the same construction as that of the semiconductor photodiode 52 and an operational amplifier 56 for amplifying the output signal supplied from the semiconductor photodiode 55.

FIG. 8 is a circuit diagram showing the electrical connection of the semiconductor laser diode 51, semiconductor photodiodes 52, 55, operational amplifiers 53, 56 and temperature variation compensating diode 54. In the light emitting portion 40, there is further provided a semiconductor photodiode 57 which receives a part of the laser light emitted from the semiconductor laser diode 41. Output signals from the semiconductor photodiode 57 and temperature variation compensating diode 54 are supplied to a differential amplifier 61 to derive a difference therebetween as a control signal. The control signal thus derived is supplied to an automatic power control circuit 62 whose output signal is supplied to the semiconductor laser diode 51. In this manner, the intensity of the infra-red laser light emitted from the semiconductor laser diode 51 can be remained constant in regardless of the temperature variation. The output signal of the semiconductor photodiodes 52 which receives the laser light transmitted through the test liquid is amplified by the first operational amplifier 53, and the output signal of the temperature variation compensating semiconductor photodiode 55 is amplified by the second operational amplifier 56. The output signals from these operational amplifiers 53 and 56 are supplied to a differential amplifier 63 provided in the controller unit 32 to derive a difference therebetween. According to the invention, the semiconductor photodiodes 52, 55 and operational amplifiers 53, 56 are arranged in the same housing 42, so that the operation temperatures of these elements are always identical with each other, and thus the temperature drift in the output signal from the differential amplifier 63 is canceled out. The output signal from the differential amplifier is processed in a measuring circuit 64 to derive the turbidity which is displayed on a display device 65.

In FIG. 9A, a curve A represents a relationship between the temperature and the output of the semiconductor photodiode 52 when the laser light having the constant intensity is made incident upon the semiconductor photodiode, and curve B shows the relationship between the temperature and the output of the semiconductor photodiode 55 which is shielded from the external light. The output from the semiconductor photodiode 55, i.e. the dark current increases in accordance with the increase of the temperature, so that the output of the semiconductor photodiode 52 also increases in proportion to the temperature. Therefore, the output of the semiconductor photodiode 52 might be detected as if the intensity of the incident laser light increases. According to the invention, the outputs of the semiconductor photodiodes 52 and 56 are amplified by the operational amplifiers 53 and 56, respectively and then the difference between the amplified outputs is derived by the differential amplifier 63, so that the output of the differential amplifier becomes constant in regardless of the temperature change as illustrated by a curve A in FIG. 9B.

In FIG. 10, a curve A represents an error in the optical density (OD) value measured by the photometering apparatus shown in FIG. 1A in which the difference between the output signals of the temperature compensating semiconductor photodiode 2 and the measuring semiconductor photodiode 1 is derived by the differential amplifier 4. The error in the OD value increased in accordance with the increase of the temperature in a non-linear manner. This is mainly due to the temperature drift of the differential amplifier 4. A graph B in FIG. 10 represents the error in the OD value measured by the photometering apparatus according to the invention. The error in the OD value changes linearly. There is remained a very small error in the OD value due to the difference in the property and operation temperature between the semiconductor photodiodes 52 and 53. However, the error is smaller than 0.01 over the measuring temperature range, the very high precision up to the third order below the decimal point can be attained and the small change of the turbidity during a short time period can be measured accurately.

In the embodiment explained above, since the coarse and fine meshes are arranged in the openings 34a, 34b and 34c, air bubbles are hardly introduced into the measuring light path and any bubbles intruded in the optical can be promptly removed therefrom. Therefore, the stable measurement can be carried out for a very long time period.

Further, the semiconductor laser diode 51 and semiconductor photodiodes 52, 55 are separated from the test liquid by means of the elongated prisms 38 and 39 having the low thermal conductivity, and therefore these elements are not affected by heat as long as the temperature of the test liquid is lower than 50° C. In case of sterilizing the fermentation apparatus with the aid of the hot steam, the above elements are heated to about 130° C., but during the sterilization the elements are not energized, so that the elements are not broken. Therefore, the fermentation apparatus can be sterilized while the turbidimeter is remained to be fixed to the fermentation apparatus.

The present invention is not limited to the embodiment explained above, but many modifications and alternations may be conceived by those skilled in the art within the scope of the invention. For instance, in the above mentioned embodiments, the light emitting portion and light receiving portion are arranged in the same housing, but they may be provided in different housings as illustrated in FIG. 11. In FIG. 11, a housing 71 made of metal has an opening 71a, and in the housing there is arranged a printed circuit board 75 on which there are arranged a light receiving element 72 receiving light passing through the hole 71a and a temperature compensating light emitting element 74 which is shielded from the external light by means of a shielding wall 73. To the printed circuit board 75 there are also secured operational amplifiers 76 and 77 for amplifying outputs of the light receiving elements 72 and 74, respectively. The operational amplifiers 76 and 78 are connectable to the external circuit by means of pins 78.

In the above embodiments, the photometering apparatus according to the invention is applied to the turbidimeter, but the present invention may be equally applied to various apparatuses such as a colorimeter and an apparatus for measuring the concentration of fine particles suspended in the air.

As explained above in detail, in the photometering apparatus according to the invention, the temperature compensating light receiving element having the same construction as that of the measuring light receiving element is arranged in the same housing as that in which the measuring light receiving element is arranged, and after the outputs of the light receiving elements are amplified by the operational amplifiers having the same construction and arranged in the same housing, the amplified outputs are supplied to the differential amplifier to derive the difference therebetween. Therefore, the temperature drifts of these light receiving elements and operational amplifiers can be mutually canceled out. Further, the output impedance of the operational amplifiers are low, so that the signal cable connected between the operational amplifiers and the differential amplifier hardly picks-up the noise and thus it is possible to obtain the measured signal having high S/N value.

What is claimed is:

1. In a photometering apparatus including a light emitting portion having a light emitting element for projecting a radiation beam to a substance to be measured, and a light receiving portion having a first light receiving element for receiving radiation emanating from the substance and converting it into an electric signal, the improvement comprising a second light receiving element which has the same construction as that of the first light receiving element; a housing in which said first and second light receiving elements are installed such that the first light receiving element receives the radiation emanating from the substance, but the second light receiving element does not receive said radiation; first and second operational amplifiers having the same construction and being arranged in said housing, said first and second operational amplifiers being connected to receive and amplify output signals from the first and second light receiving elements to derive first and second amplified output signals, respectively; and a differential amplifier arranged remote from the housing and having first and second input terminals connected to said first and second operational amplifiers and deriving a difference between said amplified first and second output signals as a photometered output signal.

2. An apparatus according to claim 1, wherein said light emitting element comprises a semiconductor laser diode emitting infra-red radiation, and said first and second light receiving elements comprise first and second semiconductor photodiodes, respectively.

3. An apparatus according to claim 2, wherein said semiconductor laser diode is arranged in said housing in which said first and second semiconductor photodiodes are arranged.

4. An apparatus according to claim 3, wherein said semiconductor laser diode and first semiconductor photodiode are inserted in first and second through holes formed in the housing and said second semi-conductor photodiode is inserted in a first blind hole formed in said housing.

5. An apparatus according to claim 4, further comprising a third semiconductor photodiode arranged in the housing such that the third semiconductor photodiode receives a part of the infra-red radiation emitted from the semiconductor laser diode, a fourth semiconductor photodiode arranged in a second blind hole formed in the housing near said first through hole, a second differential amplifier arranged remote from the housing and deriving a difference between output signals supplied from said third and fourth semiconductor photodiodes, and an automatic power control circuit for receiving said difference from the second differential amplifier as a control signal to energize the semiconductor laser diode such that the intensity of the infra-red radiation emitted from the semiconductor laser diode is kept constant.

6. An apparatus according to claim 4, wherein said housing is made of metal having the good thermal conductivity.

7. An apparatus according to claim 2, wherein said light receiving portion comprises a metal cap having a hole, a printed circuit board arranged within the metal cap, said first and second semiconductor photodiodes and first and second operational amplifiers being secured to said printed circuit board such that the first semiconductor photodiode receives the radiation emanating from the substance to be measured and transmitted through aid hole, and a light shielding wall arranged in the metal cap such that the second semiconductor photodiode is shielded from the external light.

8. A turbidimeter for measuring the turbidity of a test liquid comprising
    a hollow main body having first and second ends with at least one opening located at the first end, said main body being immersible in said test liquid to permit said test liquid to enter said main body through said opening;
    a semiconductor laser diode mounted within said main body at said second main body at said second end for emitting an infra-red laser light beam;
    a first light guide member made of light transmitting and heat insulating material, said first light guide member being arranged within said main body for guiding the laser light beam emitted by said semiconductor laser diode into the first end of said main body and making said laser light beam incident upon the test liquid within said main body;
    a second light guide member made of light transmitting and heat insulating material, said second light guide member being arranged within said main body for guiding light emanating from the test liquid within said main body into the second end thereof;
    a first semiconductor photodiode arranged within said main body at said second end for receiving the light emanating from said second light guide member, said first semiconductor photodiode producing a first output signal corresponding to the turbidity of the test liquid;

a second semiconductor photodiode having the same construction as that of the first semiconductor photodiode and arranged within said main body at said second end such that the second semiconductor photodiode is shielded from light and generates a second output signal corresponding to the dark current;

first and second operational amplifiers having the same construction and arranged within said main body at said second end for amplifying said first and second output signals, respectively to derive first and second amplified output signals; and a differential amplifier arranged remote from said main body and deriving a difference between said first and second amplified output signals.

9. A turbidimeter according to claim 8, wherein said first and second light guide members are formed by first and second prisms made of glass.

10. A turbidimeter according to claim 8, wherein said semiconductor laser diode and said first and second semiconductor photodiodes are arranged in the same housing made of heat conducting material.

11. A turbidimeter according to claim 9, wherein said housing has a first through hole in which said semiconductor laser diode is inserted, a second through hole in which said first semiconductor photodiode is inserted, and a blind hole in which said second semiconductor photodiode is inserted.

12. A turbidimeter according to claim 8, further comprising an outer fine mesh and an inner coarse mesh arranged one upon the other in said opening formed in the main body.

* * * * *